United States Patent [19]

Kitamura

[11] Patent Number: 4,911,357
[45] Date of Patent: Mar. 27, 1990

[54] HUMIDITY CONTROLLER UTILIZING ABSOLUTE HUMIDITY

[75] Inventor: Kenzo Kitamura, Tokyo, Japan

[73] Assignee: Shibaura Electronics Company, Ltd., Saitama, Japan

[21] Appl. No.: 330,624

[22] Filed: Mar. 30, 1989

[30] Foreign Application Priority Data

Apr. 11, 1988 [JP] Japan .................................. 63-88661
Aug. 19, 1988 [JP] Japan ............................... 63-108942

[51] Int. Cl.⁴ .............................................. B01F 3/02
[52] U.S. Cl. .................................. 236/44 E; 73/336.5; 62/176 G
[58] Field of Search .................... 62/176 G; 236/44 C, 236/44 E; 73/336.5; 324/65 R; 340/602; 165/20

[56] References Cited

U.S. PATENT DOCUMENTS 4,419,888 12/1983 Kitamura et al. .................. 73/336.5
4,658,120 4/1987 Fujikawa ........................... 324/65 R
4,750,545 6/1988 Hile et al. ............................. 165/20

*Primary Examiner*—William E. Wayner
*Attorney, Agent, or Firm*—Helfgott & Karas

[57] ABSTRACT

In a humidity measuring part a thermistor or similar temperature sensing element is used, as a humidity sensing element, in a heated state and an electric signal of humidity is obtained as a function of absolute humidity proportional to the water content of the atmosphere in a constant temperature and humidity bath through utilization of a change in the thermal conductivity of moist air. The absolute humidity signal and an absolute humidity set value or a set value of absolute humidity converted from a relative humidity set value through use of a temperature set value are compared, and a humidity control signal is produced in accordance with the result of this comparison. A forced humidifying signal is generated upon turning ON of the power supply, and the generation of this signal is stopped upon occurrence of the humidity control signal. By this, the absolute humidity is controlled to the set value in the range above absolute humidity corresponding to a maximum point of an absolute humidity versus humidity measuring apart electric output curve. The above-mentioned absolute humidity measured and set values are compared and the humidity control signal is produced in accordance with the difference therebetween. Temperature measured and set values are compared and a temperature control signal is produced in accordance with the difference therebetween. The humidity control signal and the temperature control signal thus obtained are used to control the temperature and absolute humidity independently of each other in the ranges above and below the maximum point.

4 Claims, 10 Drawing Sheets

FIG.4

| REGION I TEMPERATURE 100°C | | REGION II POLARITY POSITIVE TEMPERATURE 100°C | | REGION II POLARITY NEGATIVE TEMPERATURE 100°C | |
|---|---|---|---|---|---|
| g/m³ | mV | g/m³ | mV | g/m³ | mV |
| 0.000 | 0.0000 | 140.00 | 10.5821 | 345.05 | 0.0000 |
| 10.000 | 1.4594 | 145.00 | 10.5754 | 350.00 | −0.4903 |
| 20.000 | 2.8106 | 150.00 | 10.5561 | 360.00 | −1.4972 |
| 30.000 | 4.0535 | 155.00 | 10.5243 | 370.00 | −2.5251 |
| 40.000 | 5.1882 | 160.00 | 10.4799 | 380.00 | −3.5739 |
| 50.000 | 6.2146 | 165.00 | 10.4230 | 390.00 | −4.6435 |
| 60.000 | 7.1329 | 170.00 | 10.3534 | 400.00 | −5.7341 |
| 70.000 | 7.9428 | 175.00 | 10.2714 | 410.00 | −6.8455 |
| 80.000 | 8.6446 | 180.00 | 10.1767 | 420.00 | −7.9779 |
| 90.000 | 9.2381 | 185.00 | 10.0695 | 430.00 | −9.1311 |
| 100.000 | 9.7233 | 190.00 | 9.9497 | 440.00 | −10.3053 |
| 110.000 | 10.1004 | 195.00 | 9.8174 | 450.00 | −11.5003 |
| 120.000 | 10.3692 | 200.00 | 9.6725 | 460.00 | −12.7162 |
| 130.000 | 10.5297 | 205.00 | 9.5150 | 470.00 | −13.9531 |
| 140.000 | 10.5821 | 210.00 | 9.3450 | 480.00 | −15.2108 |
| | | 215.00 | 9.1624 | 490.00 | −16.4894 |
| | | 220.00 | 8.9672 | 500.00 | −17.7890 |
| | | 225.00 | 8.7595 | 510.00 | −19.1094 |
| | | 230.00 | 8.5392 | 520.00 | −20.4507 |
| | | 235.00 | 8.3063 | 530.00 | −21.8129 |
| | | 240.00 | 8.0609 | 540.00 | −23.1961 |
| | | 245.00 | 7.8029 | 550.00 | −24.6001 |
| | | 250.00 | 7.5323 | 560.00 | −26.0250 |
| | | 255.00 | 7.2492 | 570.00 | −27.4708 |
| | | 260.00 | 6.9536 | 580.00 | −28.9375 |
| | | 265.00 | 6.6453 | 588.58 | −30.2126 |
| | | 270.00 | 6.3245 | | |
| | | 275.00 | 5.9911 | | |
| | | 280.00 | 5.6452 | | |
| | | 285.00 | 5.2867 | | |
| | | 290.00 | 4.9156 | | |
| | | 295.00 | 4.5320 | | |
| | | 300.00 | 4.1358 | | |
| | | 305.00 | 3.7270 | | |
| | | 310.00 | 3.3057 | | |
| | | 315.00 | 2.8718 | | |
| | | 320.00 | 2.4254 | | |
| | | 325.00 | 1.9664 | | |
| | | 330.00 | 1.4948 | | |
| | | 335.00 | 1.0106 | | |
| | | 340.00 | 0.5139 | | |
| | | 345.00 | 0.0046 | | |
| | | 345.05 | 0.0000 | | |

| SENSOR OUTPUT \ HUMIDIFYING SIGNAL | ON | OFF |
|---|---|---|
| INCREASE | I | II |
| DECREASE | II | I |

FIG. 6

| TEMPERATURE t (°C) | SATURATION WATER VAPOR PRESSURE es (Pa) | SATURATION ABSOLUTE HUMIDITY xs (g/m$^3$) |
|---|---|---|
| 0 | 610.66 | 4.846 |
| 10 | 1227.4 | 9.395 |
| 20 | 2338.1 | 17.287 |
| 30 | 4244.9 | 30.350 |
| 40 | 7381.2 | 51.089 |
| 50 | 12345 | 82.803 |
| 60 | 19934 | 129.693 |
| 62 | 21853 | 141.330 |
| 70 | 31179 | 196.944 |
| 80 | 47377 | 290.787 |
| 90 | 70121 | 418.535 |
| 100 | 101325 | 588.580 |

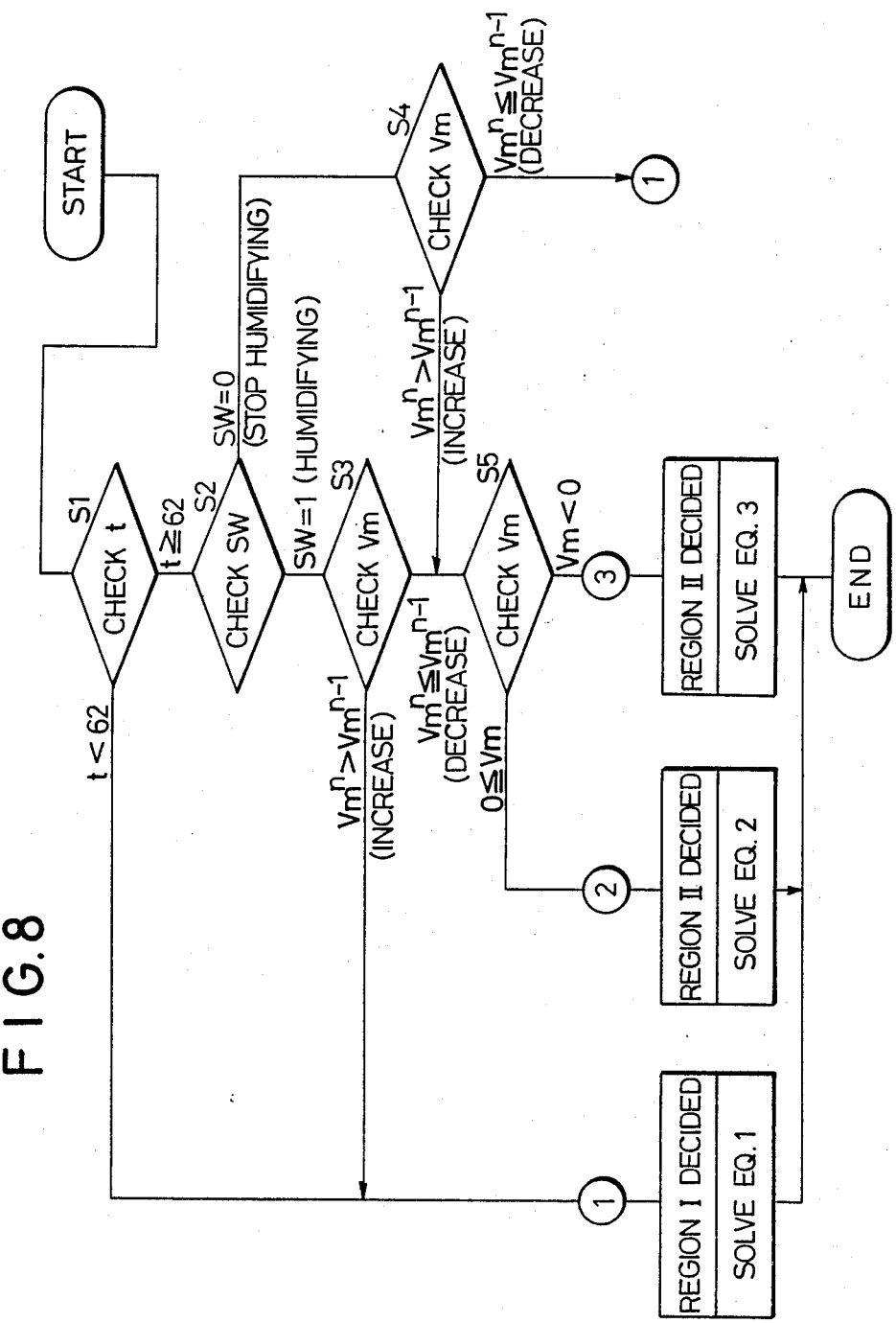
F I G. 8

HUMIDITY CONTROLLER UTILIZING ABSOLUTE HUMIDITY

BACKGROUND OF THE INVENTION

1. Field of the Invention

The present invention relates to a temperature and humidity controller for a constant temperature and humidity bath and, more particularly, to a temperature and humidity controller which is suitable for use with a constant temperature and humidity under high temperature and high humidity conditions.

2. Description of the Prior Art

Many kinds of constant temperature and humidity baths are now on the market as environmental test equipment for making temperature and humidity characteristics tests of electronic parts and various materials.

Conventionally, a psychrometer of the type including temperature sensors such as platinum resistance bulbs, thermocouples, or thermistors are employed as a humidity sensor for effecting humidity control in such a constant temperature and humidity bath, and in general, relative humidity is computed from the temperature difference between the dry and the wet bulb so that humidity control is effected accordingly. The humidity computing method by such a psychrometric method is known as defined under JIS (Japanese Industrial Standard) 8806.

Humidity sensors of other than the psychrometer are, for example, resistive and capacitive humidity sensors which utilize variations in their electrical characteristics which are caused by adsorption. They include an electrolytic lithium chloride humidity sensor, an organic high polymer film humidity sensor, a metallic oxide ceramics humidity sensor, etc.

A constant temperature and humidity bath control method employing such a humidity sensor is usually one that converts temperature signals of the dry and wet bulbs into a relative humidity signal and uses this signal to control the relative humidity in the bath.

Recent environmental test equipment is often required to withstand severe conditions of high temperature and high humidity. On this account, the conventional humidity sensors of the type utilizing the electrical characteristic variations by adsorption are scarcely used as the humidity sensor in the constant temperature and humidity bath, because they are not reliable in reproducibility, stability, responsibility, and interchangeability.

It is therefore a general practice in the art to employ the psychrometer as the humidity sensor in the constant temperature and humidity bath. However, the psychrometer necessitates the use of gauze and water in the wet bulb, and hence is most likely to make an error owing to strains on the gauze and fur on the wet bulb surface; accordingly, the psychrometer must be handled with the utmost care and its maintenance is very cumbersome. Besides, the conventional psychrometer has the shortcoming that an error tends to increase in a region of low temperature and low humidity.

Furthermore, it has recently been noted that the prior art method of converting temperature signals of the dry and wet bulbs into a relative humidity signal for controlling the relative humidity in the bath is not relaible, because both of the dry and wet bulb temperatures exert influence on the relative humidity control. As a solution to this problem, a method which effects control through the combined use of dew point and temperature or absolute humidity and temperature is now under study.

SUMMARY OF THE INVENTION

It is a primary object of the present invention to provide a humidity controller for a constant temperature and humidity bath with which it is possible to accurately control the humidity of the bath through independent control of its temperature and humidity by use of a temperature sensor and a absolute humidity sensor.

Another object of the present invention is to provide an absolute humidity controller of a limited range of humidity control for a constant humidity bath which operates only in a second region of absolute humidity for controlling the absolute humidity through use of relatively simple analog circuitry.

Yet another object of the present invention is to provide a humidity controller for a constant temperature and humidity bath which independently controls the temperature and humidity of the bath in both of first and second regions of absolute humidity through utilization of a microcomputer.

The absolute humidity controller of the present invention is intended for use in a constant humidity bath of the type that is provided with a humidity sensing element which has a temperature sensing element held in contact with the atmosphere in the bath and a temperature sensing element held out of contact with the atmosphere and measures absolute humidity on the basis of variations in the theremal conductivity of the atmosphere. The absolute humidity controller includes a comparator which yields a humidifying signal when the output of the humidity sensing element exceeds a preset value, a forced humidifying signal generator which is set upon turning ON of the power supply and generates a forced humidifying signal and is reset by the humidifying signal, and a humidifier driver which produces a humidifier drive signal in response to an OR signal of the humidifying signal and the forced humidifying signal. The humidifier drive signal is applied to a humidifier to cause it to humidify the interior of the constant humidity bath. The forced humidifying signal generator is put in the above-mentioned set state when a door of the constant humidity bath is opened, and the resetting of this circuit by the humidifying signal is prohibited for a certain period of time when the power source is turned ON.

The humidity controller of the present invention for use with a constant temperature and humidity bath includes for temperature measuring part which converts a signal from a temperature sensor provided in the bath to an electrical signal and then to a signal of temperature, a humidity measuring part which converts a signal from a humidity sensor provided in the bath to an electrical signal and then to a signal of absolute humidity, a setting part for setting temperature and absolute or relative humidity, a temperature control part which compares the temperature measured by the temperature measuring part and the temperature set in the temperature setting part and generates a temperature control signal accordingly, heating means for heating the bath in response to the temperature control signal, and a humidity control part which compares the humidity measured by the humidity measuring part and the humidity set in the humidity setting part and generates a humidity control signal accordingly.

In the humidity controller of the present invention a thermistor, platinum resistance bulb, or similar temperature sensor is used as the humidity sensor and held in an electrically heated state and a change in the thermal conductivity of air due to the water vapor content in the constant temperature and humidity bath is sensed as a temperature change of the sensor to thereby obtain the absolute humidity signal. This humidity measuring method has already been proposed by the applicant of this application (Japanese patent application No. 74858/79 entitled "Humidity Measuring Method" and Japanese Utility Model Application No. 81092/79 entitled "Absolute Hygrometer". The above Japanese patent applications correspond to U.S. application Ser. No. 148,465 which matured into U.S. Pat. No. 4,419,888.

The absolute humidity controller of the analog system according to the present invention which operates only in the second region of absolute humidity effects humidity control in the constant humidity bath of high temperature and humidity by humidifying it with a humidifier under control of the forced humidifying signal generator made up of an output level holding circuit for holding absolute humidity at a desired value and a forced humidifying circuit.

In the humidity controller of the present invention which utilizes a microcomputer, absolute humidity control signal is obtained by comparing the set value of absolute humidity and the value of absolute humidity sensed by the humidity sensor and, in the case of relative humidity being set, absolute humidity is obtained by computing from set values of temperature and relative humidity, then the absolute humidity value thus obtained is compared, as a set value, with the absolute humidity signal from the humidity sensor, controlling the absolute humidity accordingly.

BRIEF DESCRIPTION OF THE DRAWINGS

FIG. 4 is a table showing sensor output voltage values (mV) for absolute humidity (g/m$^3$) at an atmospheric temperature of 100° C;

FIG. 6 is a table showing the relationship between temperature and saturation absolute humidity;

FIG. 8 is a flowchart for explaining the operation of an absolute humidity characteristic region judging part;

DESCRIPTION OF THE PREFERRED EMBODIMENTS

The present invention will hereinafter be described in connection with the case where thermistors are employed as temperature sensing elements.

Figure 2:
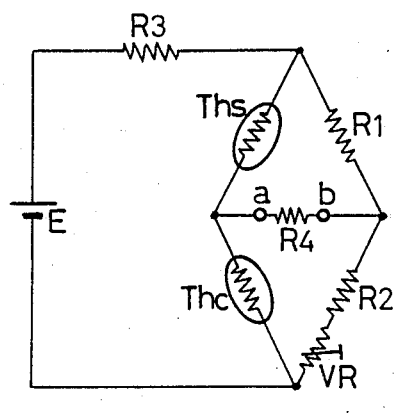
FIG. 2 is a diagram schematically showing a basic circuit arrangement for detecting absolute humidity by a humidity sensor due to thermal conduction.

FIG. 2 shows the circuit arrangement of the absolute humidity sensor for use in the present invention. Reference character E indicates the power supply, $R_1$ to $R_4$ fixed resistors, Ths a thermistor for humidity sensing use, Thc a thermistor for temperature compensation use, and a and b output terminals.

The thermistor Ths is to sense absolute humidity and is held in a vessel a with an air hole through which it is exposed to the open air. The thermistor Thc is to perform temperature compensation for measured humidity, and this thermistor is identical in structure and in characteristic with the humidity sensing thermistor Ths and is held in a perfectly dried stage in a vessel b with no air hole. The fixed resistors $R_1$ and $R_2$ are combined with the humidity sensing thermistor Ths and the temperature compensating thermistor Thc to form a bridge circuit. The bridge circuit is supplied with current from the power supply E via the fixed resistor $R_3$ for current limiting use, by which the thermistors Ths and Thc are heated to and held at around 200° C.

If now the humidity sensing thermistor Ths is placed in a perfectly dried atmosphere, the bridge circuit is in the state of equilibrium, producing no output voltage Vm across the terminals a and b. When the humidity sensing thermistor Ths is placed in an atmosphere containing water vapor, that is, in moist air, a change in the thermal conductivity of the atmosphere causes a change in the temperature of the thermistor Ths and also in its resistance, and consequently, the bridge circuit comes out of balance, yielding an output voltage Vm across the fixed resistance $R_4$. A change in the amount of water vapor in the atmosphere causes a change its thermal conductivity. In this way, the output voltage can be obtained as a function of the water vapor content of the atmosphere, i.e. absolute humidity (g/m$^3$) and temperature (° C.).

Figure 3:
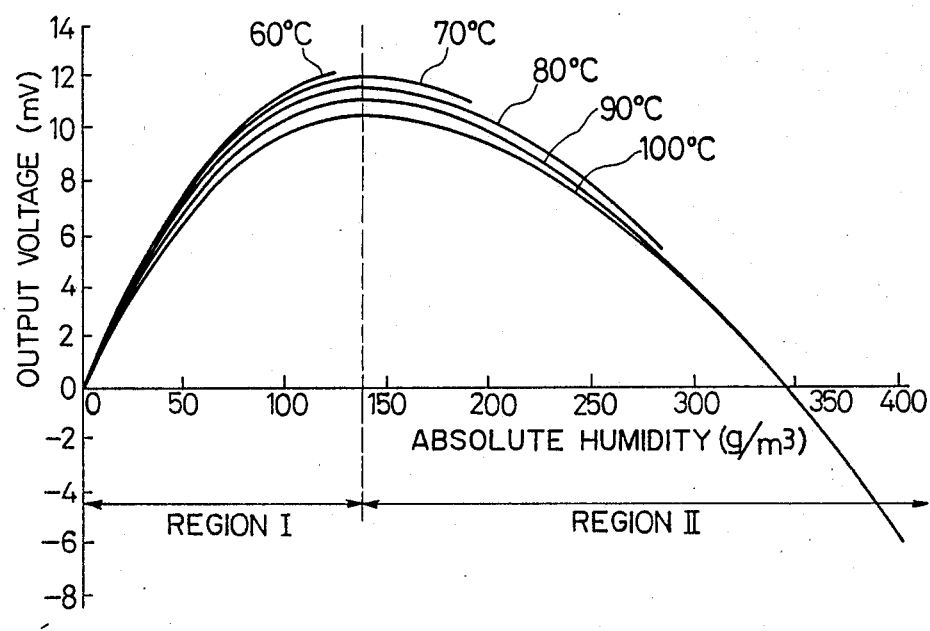
FIG. 3 is a graph showing examples of a bridge output voltage (mV) versus absolute humidity (g/m$^3$) characteristics obtained at the time of measuring absolute humidity by the humidity sensor shown in FIG. 2.

FIG. 3 shows, by way of example, the bridge output voltage Vm (mV) versus absolute humidity (g/m$^3$) characteristic of the absolute humidity sensor of FIG. 2, measured at respective temperatures until humidity was saturated.

FIG. 4 shows, as an example of the output characteristic of the absolute humidity sensor depicted in FIG. 2, its output voltages calculated from experimental results in respect of respective absolute humidity at am atmosphere temperature of 100° C.

As shown in FIG. 3, in the case of an atmosphere below 62° C., the characteristic curve forms a parabolically increasing curve from zero humidity until humidity is saturated. With an atmosphere above 62° C., however, the output voltage reaches a maximum value in the vicinity of absolute humidity 140 g/cm$^3$, and as the absolute humidity further increases, the output voltage decreases, then its polarity reverses when the absolute humidity exceeds 345 g/m$^3$. This phenomenon was found out experimentally by the inventors of this application ("Humidity Measurement", The Japan Society of Applied Physics (Yamanashi University), April 3, 1980 and "Output Characteristics of Humidity Sensor", 20th SICE Lecture (Tohoku University), July 1981). With respect to this phenomenon, however, the relationship between the amount of water vapor and the physical value of a gas containing it has not been theorized yet.

In the case of employing the absolute humidity sensor with such characteristics as shown in FIG. 3, there are two absolute humidity values corresponding to the same bridge output voltage when the atmosphere temperature is above 62° C.

Figure 1:
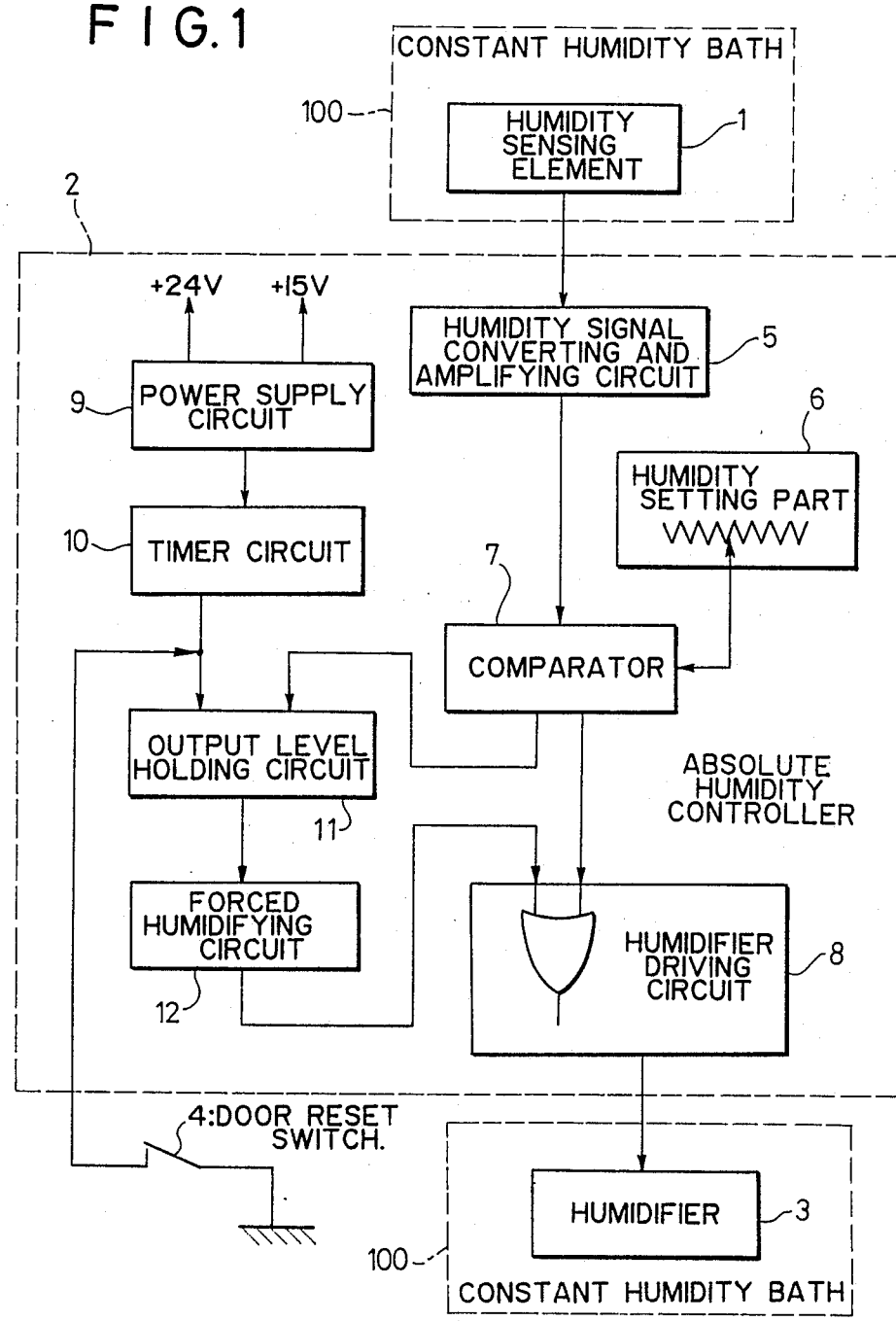
FIG. 1 is a block diagram illustrating a first embodiment of the present invention.

In FIG. 1 reference numeral 1 indicates a humidity sensing element, which is provided in a constant humidity bath 100. Reference numeral 2 designates generally the absolute humidity controller of the present invention, 3 a humidifier which is placed in the constant humidity bath 100, and 4 a door reset switch of the bath 100.

The humidity sensor 1 has a construction in which the thermistor Ths (the humidity sensing element) and the thermistor Thc (the temperature compensating element), such as depicted in FIG. 2, are integrated on a substratum.

In the absolute humidity controller 2 a humidity signal converting and amplifying circuit 5 has packaged therein the fixed resistors $R_1$ and $R_2$ forming a bridge circuit depicted in FIG. 2, the fixed resistor $R_2$ including a variable resistor Rv for zero adjustment. An electrical signal corresponding to absolute humidity, produced by such a humidity sensor, is amplified and then output.

A humidity setting part 6 has setting means formed by a variable resistor, for example, and yields an electrical signal corresponding to the humidity to be set.

A comparator 7 compares the electrical signal from the humidity signal converting and amplifying circuit 5, representing the measured humidity value, and the electrical signal from the humidity setting part 6, representing the humidity value set therein, and yields a high- or low-level signal depending on which of the measured and set values is greater.

A humidifier driver 8 has an OR circuit at its input and applies a humidifier control signal to the humidifier 3 in accordance with the high-level signal from the comparator 7 and a high-level signal from a forced humidifying circuit 12.

In the humidifier 3 its internal power supply circuit responds to the humidifier control signal to drive a humidifying device, humidifying the constant humidity bath 100.

A power supply circuit 9 is to supply required power to respective parts of the absolute humidity controller 2.

A timer circuit 10 responds to the output from the power supply circuit 9 to generate a high-level signal for a fixed period of time (several seconds, for instance) when the power supply is connected.

An output level holding circuit 1 is set by a signal from the timer circuit 10 or door reset switch 4 and is reset by the high-level signal from the comparator 7.

The forced humidifying circuit 12 responds to the output signal from the output level holding circuit 11 to generate high-level signal.

The door reset switch 4 is interlocked with the door of the constant humidity bath 100 and is turned ON when the door is opened.

The absolute humidity controller of this embodiment performs its control operation in a region II in the output characteristic shown in FIG. 2, that is, in the range of absolute humidity above 140 g/cm$^3$. The operation of this absolute humidity controller will hereinafter be described.

Figures 5, 9:
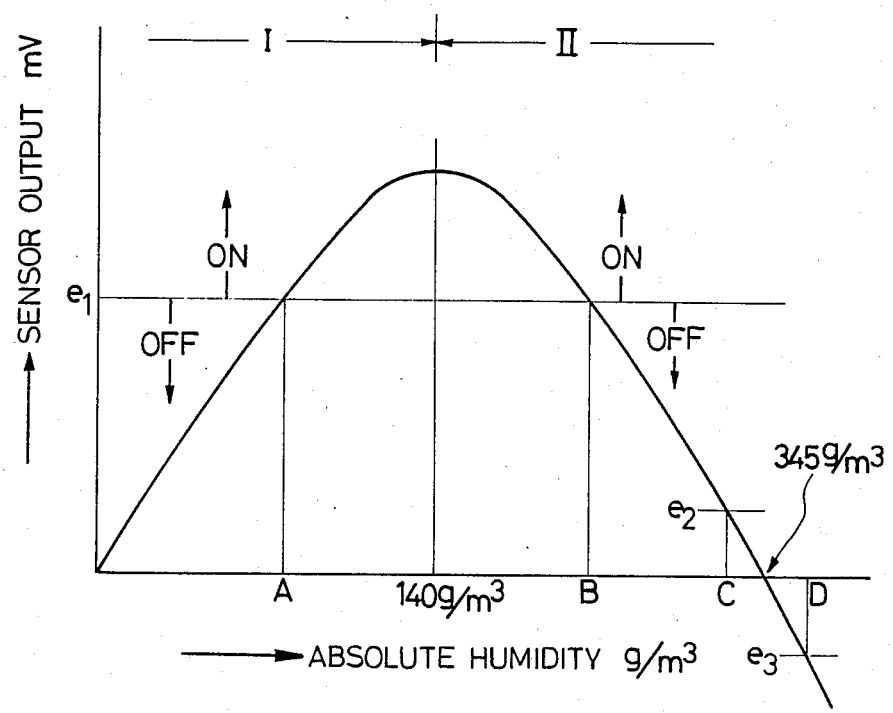
FIG. 5 is a graph for explaining the operation of the humidity controller of the present invention.
FIG. 9 is a diagram showing absolute humidity characteristic region judging logic.

As described previously, the absolute humidity sensor due to thermal conduction possesses such an absolute humidity versus output characteristic as shown in FIG. 5. Since the signal obtainable from the sensor is only its outut voltage, it is impossible to determine whether the absolute humidity corresponding to, for example, an output voltage $e_1$, is A g/cm$^3$ or B g/cm$^3$.

Now, let it be assumed that the output voltage $e_1$ corresponds to the humidity set point to which the humidity in the constant humidity bath is to be controlled. In order to effect humidity control in the region II alone, it is necessary to control the humidifier 3 to turn ON or OFF depending on whether the output from the humidity sensor is greater or smaller than the set point $e_1$, that is, whether the humidity sensed by the humidity sensor is lower or higher than B g/cm$^3$.

However, the situation occasionally arises where when the power supply is turned ON, the humidity in the bath is low, the absolute humidity is below A g/cm$^3$ in the region I and the sensor output is smaller than the set value $e_1$. In such an instance, since the comparator 7 produces a signal for turning OFF the humidifier 3 when the measured value is smaller than the set value, the humidifier 3 does not operate, and consequently, the humidity in the constant humidity bath 100 cannot be increase to B g/cm$^3$ To avoid this, when the power supply is turned ON, the output level holding circuit 11 is set by the signal from the timer circuit 10 and the forced humidifying circuit 12 is truned ON by the output signal of the output level holding circuit 11. As a result of this, the humidifier driver 8 creates a humidifier control signal, causing the humidifier 3 to perform humidification in the constant humidity bath 100.

When the humidity in the bath 100 is thus increased and exceeds A g/cm$^3$ and the sensor output becomes greater than the set value $e_1$, the comparator 7 yields a high-level signal. By this, the humidifier driver 8 is held in the ON state in which to keep on producing the high-level signal, and at the same time, the output level holding circuit 11 is reset, turning OFF the forced humidifying circuit 12. Thus the humidifier driver 8 operates solely on the signal from the comparator 7.

The humidifier 3 continues the humidifying operation and the humidity in the bath 100 further increases and enters into the region II from the region I, after which the sensor output decreases as the humidity in the bath 100 increases. When the humidity in the bath 100 further rises and exceeds B g/cm$^3$, the sensor output becomes smaller than the set value $e_1$ and the comparator 7 is turned OFF. Consequently, the humidifier 3 stops and the humidity will no longer increase.

Thereafter, when the humidity in the bath 100 gradually decreases and becomes lower than B g/cm$^3$, the sensor output exceeds the set value $e_1$ and the comparator 7 produces again the high-level signal, resuming the humidifying operation.

By such ON-OFF control which repeats the above-mentioned operation, the humidity in the constant humidity bath 100 is maintained at the value B g/cm$^3$ corresponding to the set voltage $e_1$.

Next, a description will be given of the control operation on the assumption that the humidity is set to a value C a little lower than 345 g/cm$^3$ (the sensor output voltage being $e_2$) or a value D a little higher than 345 g/cm$^3$ (the sensor output voltage being $e_3$ with a minus sign) in the region II.

In this case, since the atmosphere in the constant humidity bath 100 is at room temperature and the output voltage of the humidity sensor is higher than the set voltage $e_2$ (or $e_3$), the control operation takes place with the forced humidifying circuit 12 held in the OFF state, that is, the control operation starts in the region II. If the output voltage of the humidity sensor is higher than the set voltage, then the humidification of the bath 100 will be continued, by which the bath 100 is humidified from the beginning and the humidity gradually rises and enters into the region II from the region I. When the humidification proceeds and the output voltage of the humidity sensor becomes equal to the set voltage $e_2$ (or $e_3$), the humidifying operation is stopped and the control operation is performed at the point of the set value C g/cm$^3$ (or D g/cm$^3$), maintaining the humidity in the bath 100 at the set value. The other operations are exactly the same as those in the above-described case where the humidity is set to the value B g/cm$^3$.

The humidity in the constant humidity bath 100 will drop abruptly when its door is opened, for example. Now, assuming that the humidity in the bath 100 becomes lower than the value A g/cm$^3$, the sensor output becomes smaller than the set value $e_1$, causing the output signal of the comparator 7 to go low. Consequently, the humidifier cannot be actuated, allowing the humidity in the bath 100 to be on the decrease. To avoid this, it is necessary to restart the forced humidifying circuit 12. This embodiment employs an arrangement in which, upon opening the door of the constant humidity bath 100, the output level holding circuit 11 is set by the door reset switch 4 ganged with the door so that the forced humidifying circuit 12 yields a high-level output signal. This output signal is applied to the humidifier driver 8 to cause it to actuate the humidifier 3, performing forced humidification until the humidity B g/cm$^3$ is reached.

Upon turning ON the power supply, the timer circuit 10 is also turned ON to set the output level holding circuit 11. Since at this time the humidity sensor transiently produces a large output regardless of the humidity in the bath 100 for a short period of time until it settles down, the timer circuit 10 is adapted to create a high-level signal for this period (several seconds) so as to prevent the output level holding circuit 11 from being reset by the sensor output.

Next, a description will be given of the humidity controller of the present invention which utilizes a microcomputer and is operable in both first and second region of absolute humidity.

Supposing that the characteristic shown in FIG. 3 are standard characteristics of bridge output versus absolute humidity, the output Vm of the humidity sensor is a function of temperature t (° C.) and absolute humidity (g/cm$^3$), and hence becomes as follows:

$$Vm = f(x \cdot t)$$

In the form of an approximate expression the sensor output Vm is given as follows:

$$Vm = (Ax^2 + Bx + C) \cdot (Dt^2 + Et + F)$$

In the above expression A to F are constants which are determined by the output characteristic curves depicted in FIG. 3, and the second term $(Dt^2 + Et + F)$ is a correcting term with temperature. Put $g(t) = (Dt^2 + Et + F)$, the above expression gives the absolute humidity as follows:

$$X_1 = \frac{-B_1 + \sqrt{B_1^2 - 4A_1(C_1 - Vm/g_1(t))}}{2A_1} \quad (1)$$

$$X_2 = \frac{-B_2 + \sqrt{B_2^2 - 4A_2(C_2 - Vm/g_2(t))}}{2A_2} \quad (2)$$

$$X_3 = \frac{-B_3 - \sqrt{B_3^2 - 4A_3(C_3 - Vm)}}{2A_3} \quad (3)$$

In the above, Eq. (1) corresponds to the region I in FIG. 3 and the absolute humidity is identified by a suffix 1; Eq. (2) corresponds to the range in which the output voltage is positive in the region II, and the absolute humidity is identified by a suffix 2; and Eq. (3) corresponds to the range in which the ouput voltage is negative in the region II, and the absolute humidity is identified by a suffix 3.

FIG. 3 indicates that the bridge circuit produces a maximum output when the absolute humidity X = 140 g/cm$^3$.

FIG. 6 shows the relationship between temperature t (° C.) and saturation absolute humidity xs (g/cm$^3$). Since the absolute humidity does not exceed 140 g/cm$^3$ at temperatures below 62° C., the absolute humidity $x_1$ can be obtained using Eq. (1). When temperature goes higher than 62° C., the output voltage Vm increases until the absolute humidity reaches 140 g/cm$^3$, and the absolute humidity $x_1$ can be obtained using Eq. (1). Where temperature is above 62° C. and absolute humidity is above 140 g/cm$^3$, the output voltage Vm decreases, and consequently, the absolute humidity $x_2$ can be obtained from Eq. (2). When the humidity is higher than 345 g/cm$^3$ which is a high humidity region, the polarity of the output voltage Vm becomes minus and the absolute humidity $x_3$ can be obtained as a function of humidity alone by Eq. (3).

In constant temperature and humidity baths now in use humidity is set and displayed in terms of relative humidity in many cases. However, since it is desirable to use absolute humidity signals as the humidity control signal and the humidity sensing signal in the constant temperature and humidity bath, it is necessary to mutually convert relative humidity (%) and absolute humidity (g/cm$^3$).

Now, letting the saturation absolute humidity be represented by xs, $$xs = \frac{804}{1 + 0.00366t} \cdot \frac{es}{po} \quad (4)$$

where po is the normal atmospheric pressure, es is a saturation water vapor pressure, and t is temperature (° C.). On the other hand, relative humidity H (%) is as follows:

$$H = \frac{x}{xs} \times 100 \quad (5)$$

Accordingly, control of the constant temperature and humidity bath in terms of relative humidity can be achieved simply by controlling the absolute humidity x while utilizing the absolute humidity at that time as a target value.

The calculation for mutual conversion of relative humidity (%) and absolute humidity (g/cm$^3$) can be conducted through utilization of the relationship between the data shown in FIG. 6 and Eq. (5).

Figure 7A:
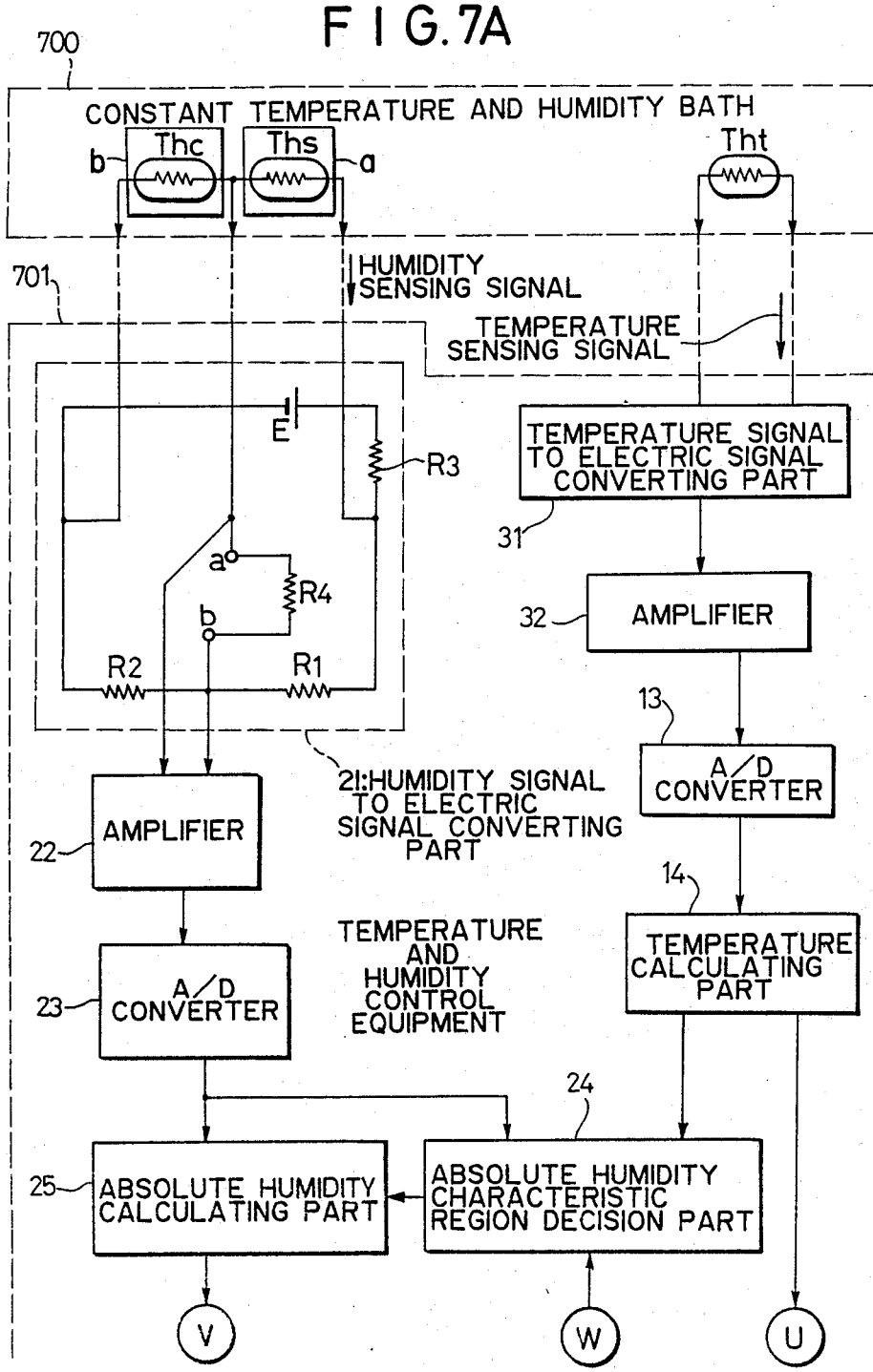
FIGS. 7A and 7B are a block diagram illustrating a second embodiment of the present invention.
Figure 7B:
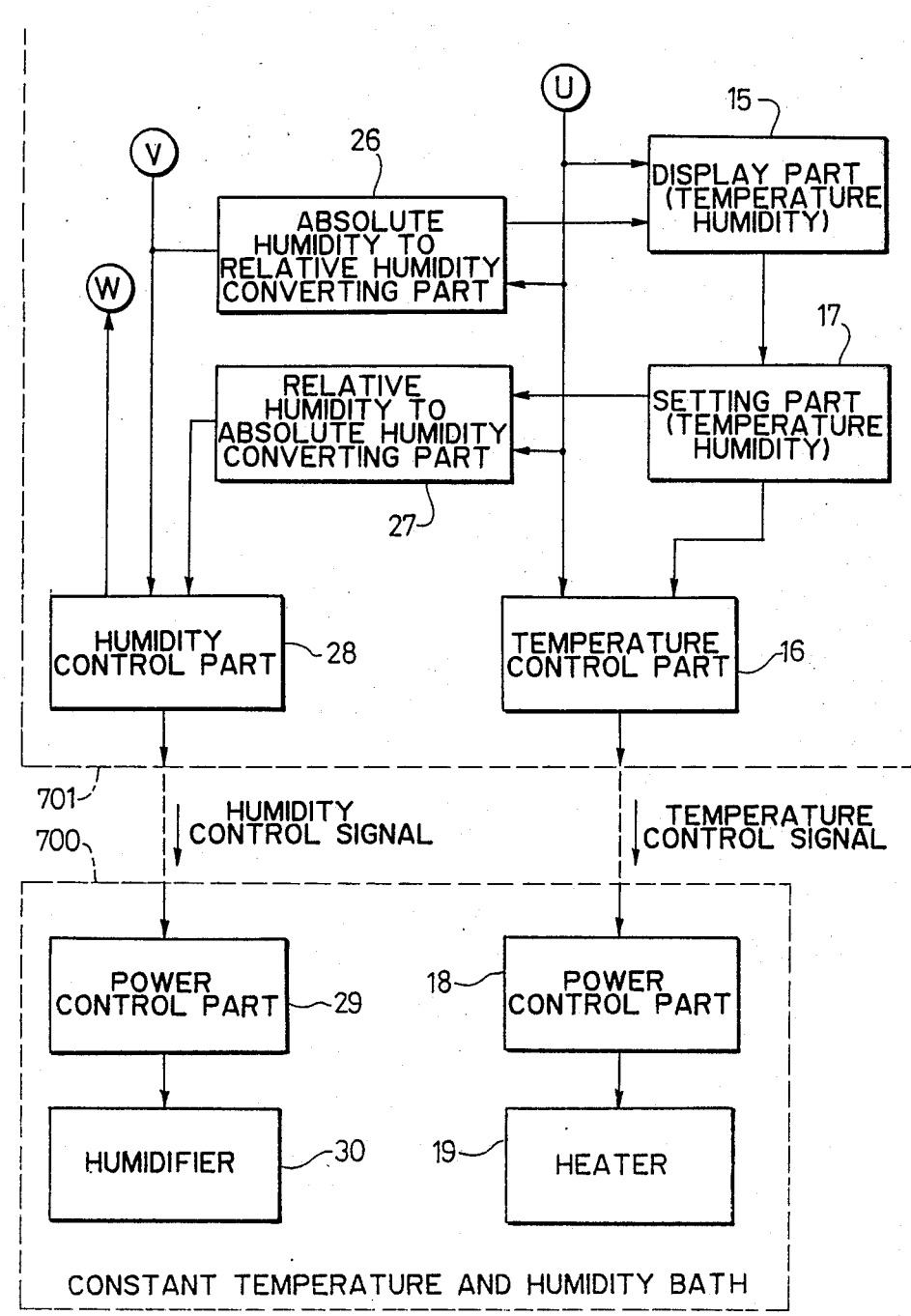

FIGS. 7A and 7B illustrate in block form a second embodiment of the present invention, which is a temperature and humidity controller, indicated generally by 701, which is adapted for setting humidity in terms of relative humidity. This embodiment employs thermistors for sensing temperature and humidity. These sensing elements are all packaged in the atmosphere in the constant temperature and humidity bath which is to be controlled, and they constitute a measuring circuit in combination with electronic circuits packaged in the temperature and humidity controller 701.

In FIGS. 7A and 7B a temperature sensing signal from the temperature sensing thermistor Tht in a constant temperature and humidity bath 700 is provided to a temperature signal to electric signal converting part 31, wherein it is converted into a voltage signal. The voltage signal is amplified by an amplifier 32 and is converted by an analog-to-digital (A/D) converter 13 into a digital signal, which is applied to a temperature calculating part 14 of a microcomputer, wherein it is used to calculate a temperature display value (° C.). This value is displayed on a display part 15 and, at the same time, it is provided to a temperature control part 16. On the other hand, there is set in a setting part (17) a target temperature to which the temperature in the constant temperature and humidity bath 700 is to be controlled. The temperature control part 16 compares the set temperature and the sensed temperature and, in accordance with the resulting error signal, effects PID control and yields a temperature control signal. A power control part 18 responds to the temperature control signal to control the power supply to a heater 19, which generates heat accordingly, raising the temperature in the constant temperature and humidity bath 700. The temperature sensing thermistor Tht senses varying temperatures, by which a cycle of temperature control is effected so that the bath temperature settles down to the set value.

Humidity sensing signals from humidity sensing thermistor Ths and a temperature compensation thermistor Thc in the constant temperature and humidity bath 700 are converted into voltage signals in a humidity signal to electric to electric signal converting part 21 which is formed by the absolute humidity sensing circuit shown in FIG. 2. The voltage signal is amplified by an amplifier 22 and is then converted by analog-to-digital (A/D) converter 23 into a digital signal. The digital signal is applied via an absolute humidity characteristic region decision part 24 to an absolute humidity calculating part 25 of the microcomputer, wherein it is used to calculated absolute humidity (g/cm$^3$). An absolute humidity to relative humidity calculating part 26 calculates relative humidity (%) on the basis of absolute humidity and temperature, and the relative humidity thus calculated is displayed on the display part 15. In the setting part 17 there is also set a target relative humidity to which the humidity in the bath 700 is to be controlled, and a relative humidity to absolute humidity converting part 27 converts the set relative humidity into absolute humidity, which is provided to a humidity control part 28. The humidity control part 28 compares the set absolute humidity and the sensed absolute humidity and, in accordance with the resulting error signal, performs PID control and yields a humidity control signal. A power control part 29 responds to the humidity control signal to turns ON and OFF the power supply to a humidifier 30, which generates water vapor accordingly, increasing the humidity in the bath 100.

The humidity sensing thermistor Ths and the temperature compensating thermistor Thc sense varying humidity, by which a cycle of humidity control is effected so that the bath humidity settles down to the set value.

In this instance, the calculations for mutual conversion of the absolute humidity and the relative humidity in the absolute humidity to relative humidity converting part 26 and the relative humidity to absolute humidity converting part 27 call for signals of temperature as seen from Eqs. (4) and (5), and the signals of temperature (° C.) are provided to these converting parts from the temperature calculating part 14.

FIG. 8 is a flowchart for explaining the operation of the absolute humidity characteristic region decision part 24. The operation starts with checking the atmospheric temperature t in the bath 700 (step S1). If $t < 62$(° C.), it is determined that the absolute humidity is in the region I below 140 g/cm$^3$, and the operation proceeds to a process (1). When $t \geq 62$(° C.), it is necessary to determine whether the absolute humidity is in the region I or II. This takes place following the logic shown in FIG. 9 through utilization of ON-OFF control of the power supply to the humidifier 30 for humidity control in this embodiment. That is, it is checked whether a switch for the power supply to the humidifier 30 in the power control part 29 is in the OFF (humidification suspended) or ON (humidifying) state (step S2). If the switch is in the humidifying state, a check is made on output voltage values $Vm^{n-1}$ (the previous measured value) and $Vm^n$ (the current measured value) of the absolute humidity sensing circuit measured at a fixed short time interval. When $Vm^n > Vm^{n-1}$ (that is, the output voltage Vm is on the increase), it is determined that the absolute humidity is in the region I, and the operation proceeds to the process (1) (step S3). If the switch is in the OFF state, then the output voltage Vm of the absolute humidity sensing circuit is checked. If $Vm^n \leq Vm^{n-1}$ (that is, the output voltage Vm is on the decrease), then it is determined that the absolute humidity is in the region I, and consequently, the operation proceeds to the process (1) (step S4). In the cases where $Vm^n \leq Vm^{n-1}$ (the output voltage being on the decrease) in step S3 and $Vm^n > Vm^{n-1}$ (the output voltage being on the increase) in step S4, it is determined that the absolute humidity is in the region II. Hence, the output voltage Vm of the absolute humidity sensing circuit is checked again, and the operation proceeds to a process (2) or (3) depending on whether $0 \leq Vm$ or $Vm < 0$ (step S5).

In the case where the operation has proceeded to the process (1) on the basis of the determination that the absolute humidity is in the region I in FIG. 3, the absolute humidity calculating part 25 solves Eq. (1) to obtain the absolute humidity $x_1$. In the case of the process (2) based on the determination that the absolute humidity is in the range of the positive output voltage in the region II in FIG. 3, the absolute humidity calculating part 25 solves Eq. (2) to obtain the absolute humidity $x_2$. In the case of the process (3) based on the determination that the absolute humidity is in the range of the negative output voltage in the region II in FIG. 3, the absolute humidity calculating aprt 25 solves Eq. (3) to obtain the absolute humidity $x_3$.

Figure 10A:
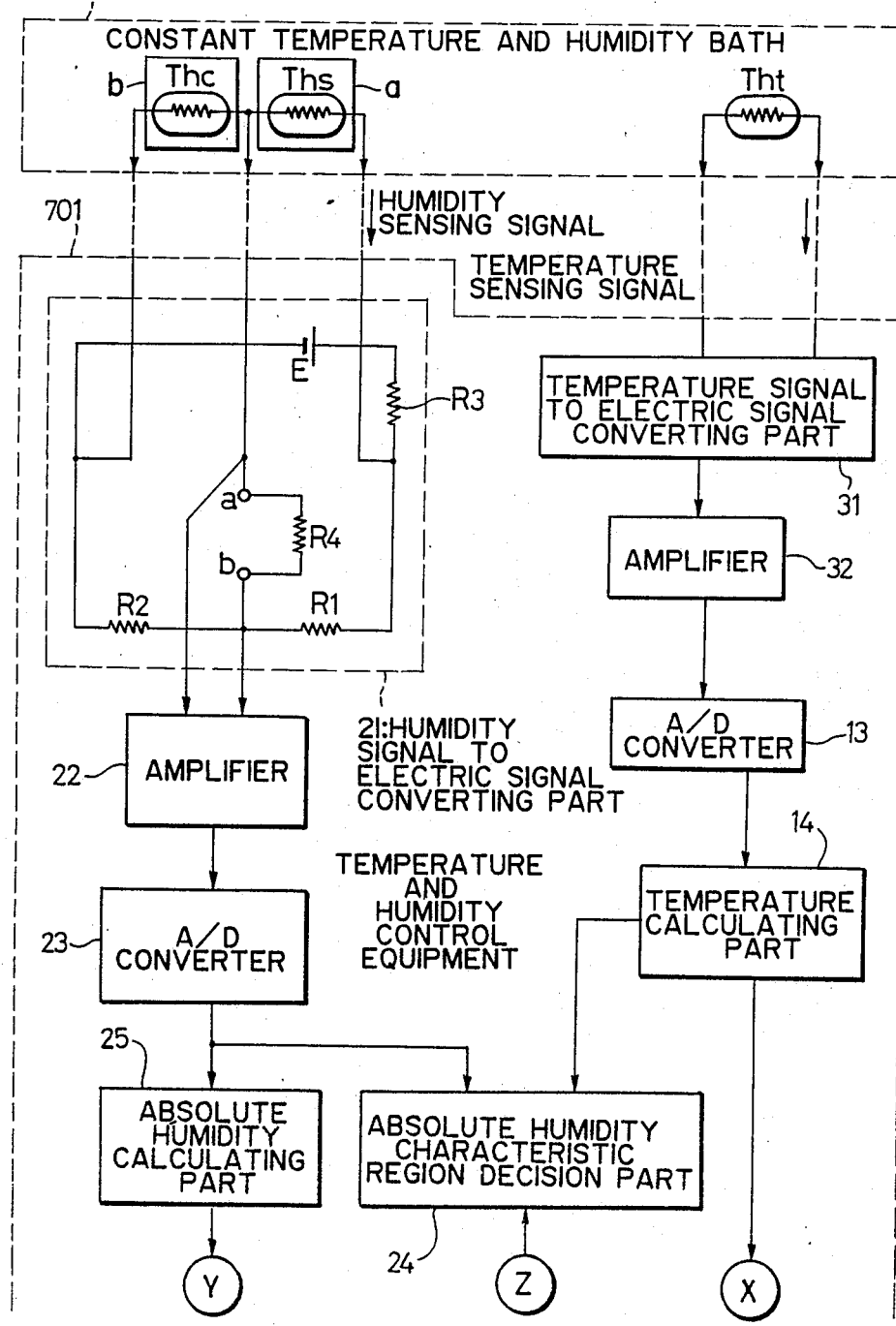
FIGS. 10A and 10B are a block diagram illustrating a third embodiment of the present invention.
Figure 10B:
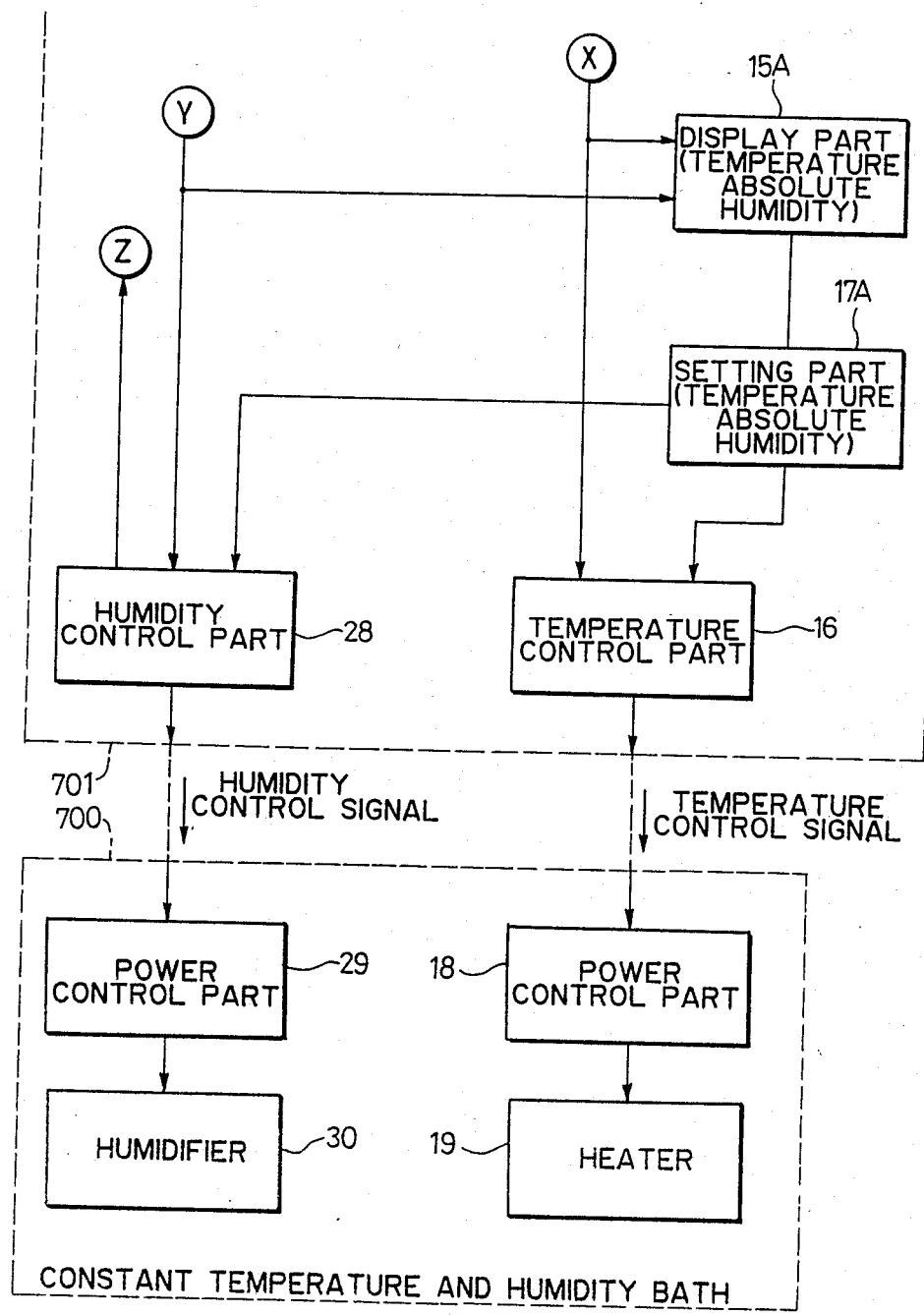

FIGS. 10A and 10B illustrate in block form a third embodiment of the present invention, in which the parts corresponding to those in FIGS. 7A and 7B are identified by the same reference numerals. Reference numeral 15 indicates a display part and 17A a setting part.

The illustrated embodiment is designed for setting and displaying humidity in terms of absolute humidity, and consequently, the humidity display in the display part 15A and the humidity setting in the setting part 17A are both provided in terms of absolute humidity. This makes unnecessary the absolute humidity to relative humidity converting part 26 and the relative humidity to absolute humidity converting part 27 in the embodiment of FIGS. 7A and 7B, permitting simplification of the circuit arrangement.

With the humidity controller of the present invention, humidity control could be achieved up to a saturation absolute humidity 588 g/cm$^3$ within the range of the bath atmospheric temperature from the vicinity of 0° C. to 100° C.

Many of conventional constant temperature and humidity baths utilize relative humidity for both of displaying and setting of humidity and employ the psychrometric method for the humidity detection. On this account, they are inevitably complex in control operation and cannot perform highly accurate control. In contrast thereto, the present invention utilizes absolute humidity for both of the humidity detection and control, and hence enables humidity control to be effected independently of temperature control, permitting highly accurate humidity control.

Moreover, the use of thermistors as humidity sensing elements makes the operation of the humidity controller stable even in an atmosphere of high temperature and high humidity and also increases its service life.

The above description has been given of two kinds of embodiments of the present invention. The former humidity controller makes it possible to control, at desired absolute humidity, the bath atmosphere whose temperature above 60° C. and whose absolute humidity is higher than 140 g/cm$^3$. Further, this humidity controller eliminates the necessity of maintenance which is needed in the psychrometric humidity control, and ensures stable control for a long period of time.

The latter absolute humidity controller employing a microcomputer allows ease in stable control of the constant temperature and humidity bath which is now being strongly demanded, and hence is suitable for use as environmental test equipment.

It will be apparent that many modifications and variations may be effected without departing from the scope of the novel concepts of the present invention.

What is claimed is:

1. An absolute humidity controller which employs, as a humidity sensing element, a thermistor or like temperature sensing element in a heated state in a humidity measuring part and obtains an electric signal of humidity as a function of absolute humidity proportional to the water content of the atmosphere in a constant humidity bath through utilization of a change in the thermal conductivity of moist air, the absolute humidity controller comprising:

an absolute humidity measuring part whereby a signal from an absolute humidity sensing element is converted into an electric signal and then into a signal of absolute humidity;

a humidity setting part for setting absolute humidity or relative humidity;

an absolute humidity calculating part whereby when humidity is set in terms of relative humidity, absolute humidity to be set is calculated on the basis of a signal of temperature from a temperature setting part and a signal of the relative humidity set in the humidity setting part;

a humidity control part which compares absolute humidity measured by the humidity measuring part and the absolute humidity set in the humidity setting part and generates a humidity control signal; and a forced humidifying signal generator which is set by turning ON the power supply to generate a forced humidifying signal and is reset by the humidity control signal from the humidity control part;

wherein the absolute humidity is controlled to the set value in the range above absolute humidity (g/cm$^3$) corresponding to a maximum point on an absolute humidity (g/cm$^3$, x axis versus humidity measuring part electric output (mV, Y axis) curve.

2. The absolute humidity controller of claim 1, wherein the forced humidifying signal generator is set when a door of the constant humidity bath is opened.

3. The absolute humidity controller of claim 1, wherein the forced humidifying signal generator is prohibited from being reset by the humidity control signal for a fixed period of time when the power supply is turned ON.

4. A humidity controller which employs, as a humidity sensing element, a thermistor or like temperature sensing element in a heated state in a humidity measuring part, obtains an electric signal of humidity as a function of absolute humidity proportional to the water content of the atmosphere in a constant temperature and humidity bath through utilization of a change in the thermal conductivity of moist air, and controls the temperature and humidity of the bath atmosphere to a desired value, the humidity controller comprising:

a temperature measuring part whereby a signal from a temperature sensing element provided in the bath is converted into an electric signal and the electric signal is further converted into a signal of temperature;

a temperature setting part for setting temperature;

a temperature control part which compares the temperature measured by the temperature meauring part and the temperature set in the temperature setting part and generates a temperature control signal;

an absolute humidity measuring part whereby a signal from an absolute humidity sensing element provided in the bath is converted into an electric signal and then into a signal of absolute humidity;

a humidity setting part for setting absolute humidity or relative humidity;

an absolute humidity calculating part whereby when humidity is set in terms of relative humidity, absolute humidity to be set is calculated on the basis of the temperature signal from the temperature setting part and a signal of the relative humidity set in the humidity setting part; and a humidity control part which compares the absolute humidity measured by the humidity measuring part and the absolute humidity set in the setting part and generates a humidity control signal;

wherein the humidity control part has means whereby it is determined whether the absolute humidity is in a first or second region of an absolute humidity region over which the absolute humidity is to be controlled, the first region being lower than absolute humidity (g/cm$^3$) corresponding to a maximum point on an absolute humidity (g/cm$^3$, X axis) versus humidity measuring part electric output (mV, Y axis) curve and the second region being higher than the absolute humidity corresponding to the maximum point; and wherein the temperature and absolute humidity in the bath are controlled independently of each other in either of the first and second regions.

* * * * *